United States Patent
Klotz et al.

(10) Patent No.: US 10,398,467 B2
(45) Date of Patent: Sep. 3, 2019

(54) SURGICAL SCALPEL AND SYSTEM PARTICULARLY FOR USE IN A TRANSVERSE CARPAL LIGAMENT SURGICAL PROCEDURE

(71) Applicant: DePuy Synthes Products, Inc., Raynham, MA (US)

(72) Inventors: Conrad Lee Klotz, Largo, FL (US); Sarah Elizabeth Carter (Stephens), Fort Wayne, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 282 days.

(21) Appl. No.: 15/486,993

(22) Filed: Apr. 13, 2017

(65) Prior Publication Data
US 2017/0215909 A1 Aug. 3, 2017

Related U.S. Application Data

(62) Division of application No. 13/762,273, filed on Feb. 7, 2013, now Pat. No. 9,636,140, which is a division
(Continued)

(51) Int. Cl.
*A61B 5/00* (2006.01)
*A61B 17/3211* (2006.01)
(Continued)

(52) U.S. Cl.
CPC .. *A61B 17/3211* (2013.01); *A61B 17/320036* (2013.01); *A61B 17/32093* (2013.01);
(Continued)

(58) Field of Classification Search
CPC .... A61B 17/320016; A61B 17/320036; A61B 17/3209; A61B 17/3211;
(Continued)

(56) References Cited

U.S. PATENT DOCUMENTS 4,509,524 A 4/1985 Miwa
4,783,867 A 11/1988 Tsao
(Continued)

OTHER PUBLICATIONS

Kinetikos Medical Incorporated (KMI), "SafeGuard-Mini Carpal Tunnel Release System," Apr. 1999 (6 pages).
(Continued)

*Primary Examiner* — Ryan J. Severson
(74) *Attorney, Agent, or Firm* — Maginot, Moore & Beck, LLP

(57) ABSTRACT

A surgical method in one method includes making an opening in the skin of a patient having an orthopedic condition involving a nerve pathology producing pain, positioning an instrument in the opening, the instrument having first and second substantially opposed arcuate arms, each arm having a concave inside surface so that the arms substantially define a rounded space, and a third component located substantially at a periphery of the rounded space, retaining an internal target tissue comprising a nerve on the instrument, causing an emitter to apply an emission signal upon the retained tissue, causing a detector to receive an evaluation signal from the internal target tissue, wherein the evaluation signal is a tissue response to the emission signal, causing a processor to receive the evaluation signal from the detector, receiving an indicia about the nerve from the processor, and retracting the third component in response to the indicia.

8 Claims, 5 Drawing Sheets

Related U.S. Application Data of application No. 10/610,474, filed on Jun. 30, 2003, now Pat. No. 8,419,728.

(51) Int. Cl.
*A61B 17/32* (2006.01)
*A61B 17/3209* (2006.01)
*A61B 17/00* (2006.01)
*A61N 1/08* (2006.01)
*A61B 90/00* (2016.01)

(52) U.S. Cl.
CPC ... *A61B 5/4893* (2013.01); *A61B 2017/00026* (2013.01); *A61B 2017/320052* (2013.01); *A61B 2090/08021* (2016.02); *A61N 1/08* (2013.01)

(58) Field of Classification Search
CPC .......... A61B 2017/00039; A61B 2017/00115; A61B 2017/00119; A61B 2017/00123; A61B 2017/320052; A61B 2017/32113; A61B 2090/0801; A61B 2090/08021; A61B 5/4893; A61N 1/08

See application file for complete search history.

(56) References Cited

U.S. PATENT DOCUMENTS

| | | | |
|---|---|---|---|
| 4,875,487 A | 10/1989 | Seppi | |
| 4,962,766 A | 10/1990 | Herzon | |
| 4,962,770 A | 10/1990 | Agee et al. | |
| 5,284,153 A | 8/1994 | Raymond et al. | |
| 5,284,154 A | 8/1994 | Raymond et al. | |
| 5,344,424 A | 9/1994 | Roberts et al. | |
| 5,423,804 A | 6/1995 | Kulick | |
| 5,445,638 A | 8/1995 | Rydell et al. | |
| 5,458,130 A | 10/1995 | Kaufman et al. | |
| 5,485,839 A | 1/1996 | Aida et al. | |
| 5,501,655 A | 3/1996 | Rolt et al. | |
| 5,527,331 A | 6/1996 | Kresch et al. | |
| 5,549,544 A | 8/1996 | Young et al. | |
| 5,569,300 A * | 10/1996 | Redmon | A61B 17/0206 600/219 |
| 5,667,473 A | 9/1997 | Finn et al. | |
| 5,722,411 A | 3/1998 | Suzuki et al. | |
| 5,775,331 A | 7/1998 | Raymond et al. | |
| 5,795,311 A | 8/1998 | Wess | |
| 5,924,999 A | 7/1999 | Agee et al. | |
| 5,928,158 A | 7/1999 | Aristides | |
| 5,954,675 A | 9/1999 | Dellagatta | |
| 5,987,346 A | 11/1999 | Benaron et al. | |
| 6,007,499 A | 12/1999 | Martin et al. | |
| 6,148,225 A | 11/2000 | Kestler et al. | |
| 6,179,852 B1 | 1/2001 | Strickland et al. | |
| 6,217,602 B1 * | 4/2001 | Redmon | A61B 17/0206 128/898 |
| 6,259,945 B1 | 7/2001 | Epstein et al. | |
| 6,312,392 B1 | 11/2001 | Herzon | |
| 6,364,849 B1 | 4/2002 | Wilcox | |
| 6,425,867 B1 | 7/2002 | Vaezy et al. | |
| 6,466,817 B1 | 10/2002 | Kaula et al. | |
| 6,488,639 B1 | 12/2002 | Ribault et al. | |
| 6,494,882 B1 | 12/2002 | Lebouitz et al. | |
| 6,500,128 B2 | 12/2002 | Marino | |
| 6,564,079 B1 | 5/2003 | Cory et al. | |
| 6,589,174 B1 | 7/2003 | Chopra et al. | |
| 6,605,078 B2 | 8/2003 | Adams | |
| 6,685,639 B1 | 2/2004 | Wang et al. | |
| 6,719,694 B2 | 4/2004 | Weng et al. | |
| 7,135,017 B2 * | 11/2006 | Klotz | A61N 7/02 606/28 |
| 7,135,029 B2 | 11/2006 | Makin et al. | |
| 8,000,782 B2 * | 8/2011 | Gharib | A61B 5/0492 600/546 |
| 8,419,728 B2 * | 4/2013 | Klotz | A61B 17/32003 606/39 |
| 9,636,140 B2 * | 5/2017 | Klotz | A61B 17/32003 |
| 2001/0039419 A1 | 11/2001 | Francischelli et al. | |
| 2003/0229343 A1 | 12/2003 | Albrecht et al. | |
| 2004/0019303 A1 | 1/2004 | Thomson | |
| 2004/0267243 A1 * | 12/2004 | Klotz | A61B 17/32003 606/1 |
| 2006/0184022 A1 | 8/2006 | Johnson | |
| 2006/0276782 A1 * | 12/2006 | Gedebou | A61B 17/32003 606/45 |
| 2013/0158575 A1 * | 6/2013 | Klotz | A61B 17/32003 606/167 |
| 2017/0215909 A1 * | 8/2017 | Klotz | A61B 17/32003 |

OTHER PUBLICATIONS

Viegas, Steven F. et al., "Extra-Bursal Technique of Endoscopic Release of the Carnal Ligament," An Illustrated Guide to the Modified Chow Technique Endoscopic Release of the Carpal Ligament, Smith & Nephew, Inc., Nov. 14, 1997 (12 pages).

Koninklijke Philips Electronics N.V., HDI 5000 Ultrasound System: Unparalleled Performance Inside and Out, Dec. 2002 (16 pages).

Agilent Technologies Healthcare Solutions Group, "Case Studies: SonoCT Real-Time Compound Imaging," Jun. 2001 (2 pages).

Agilent Technologies Healthcare Solutions Group, "Comparison of Image Clarity: SonoCT Real-Time Compound Imaging Versus Conventional 2D Ultrasound Imaging," Jun. 2001 (2 pages).

* cited by examiner

SURGICAL SCALPEL AND SYSTEM PARTICULARLY FOR USE IN A TRANSVERSE CARPAL LIGAMENT SURGICAL PROCEDURE

This is a divisional application of co-pending U.S. application Ser. No. 13/762,273, filed on Feb. 7, 2013, which issued as U.S. Pat. No. 9,636,140 on May 2, 2017, the entire disclosure of which is incorporated herein by reference, which in turn is a divisional of U.S. application Ser. No. 10/610,474, filed on Jun. 30, 2003, which issued as U.S. Pat. No. 8,419,728 on Apr. 16, 2013, the entire disclosure of which is incorporated herein by reference, which cross-references U.S. patent application Ser. No. 10/610,463, also filed on Jun. 30, 2003, entitled "Imaging and Surgical Procedure for Carpal Tunnel Syndrome" by Conrad Lee Klotz and Sarah Elizabeth Stephens (now U.S. Pat. No. 7,135,017 issued Nov. 14, 2006).

FIELD OF THE INVENTION

The present invention relates to instruments for performing surgical procedures especially ones for relieving problems associated with carpal tunnel syndrome and, more particularly, to a scalpel and/or scalpel system for use in a transverse carpal ligament surgical procedure.

BACKGROUND INFORMATION

Carpal tunnel syndrome is a common problem that affects the hand and wrist. This condition, or syndrome, has become the focus of much attention in the last few years due to suggestions that it may be linked to certain occupations that require repetitive use of the hands, such as typing. While certain occupations may experience more problems with carpal tunnel syndrome, many people develop this condition regardless of their occupation.

Particularly, carpal tunnel syndrome (CTS) is a condition that results when the median nerve of the hand does not function properly. Usually, this occurs because there is too much pressure on the median nerve that extends into the wrist through an opening called the carpal tunnel. The median nerve extends into the hand to receive sensation from the thumb, index finger, long finger, and half of the ring finger. The median nerve also provides a branch to the muscles of the thumb (i.e. the thenar muscles).

The carpal tunnel is an opening into the hand that is made up of the bones of the wrist (i.e. the carpals) on the bottom and the transverse carpal ligament on the top. The median nerve and the flexor tendons extend through the carpal tunnel into the hand. The median nerve lies just under the transverse carpal ligament. A material called the tenosynovium covers the flexor tendons. The tenosynovium is slippery and thus allows the tendons to glide against each other as they move. Any condition that causes irritation or inflammation of the tendons can result in swelling and/or thickening of the tenosynovium. As the tenosynovium begins to swell and/or thicken, pressure begins to increase in the carpal tunnel. This is because the bones and ligaments that constitute the carpel tunnel are fixed in size and thus are not able to stretch in response to the swelling. Increased pressure in the carpel tunnel begins to squeeze the median nerve against the transverse carpal ligament, since the median nerve is the softest structure in the carpal tunnel. Eventually, the pressure reaches a point where the median nerve can no longer function normally. This manifests itself as pain and numbness in the hand.

There are many conditions that can result in irritation and inflammation of the tenosynovium, and eventually cause carpal tunnel syndrome. Different types of arthritis can cause inflammation of the tenosynovium directly. A fracture of the wrist bones may later cause carpal tunnel syndrome if the healed fragments result in abnormal irritation on the flexor tendons. Particularly, anything that causes abnormal pressure on the median nerve will result in the symptoms of carpal tunnel syndrome.

In the early stages of carpal tunnel syndrome, non-operative treatments are typically used. One such non-operative treatment is the use of a brace. The brace keeps the wrist in a neutral position. When the wrist is in a neutral position, the carpal tunnel is as large as it can be so the median nerve has as much room as possible.

Another non-operative treatment that tries to reduce the symptoms of carpal tunnel syndrome is the use of anti-inflammatory medications to help control swelling of the tenosynovium. Anti-inflammatory medications include over the counter medications such as ibuprofen and aspirin, as well as high doses of vitamin B-6. Injections of cortisone into the carpal tunnel may also be used in order to decrease swelling of the tenosynovium and thereby give temporary relief of symptoms.

If the non-operative treatments fail to control the symptoms of carpal tunnel syndrome, surgery may be required to reduce the pressure on the median nerve. There are essentially three surgical techniques designed to relieve pressure on the median nerve. The first and most common surgical procedure is the traditional open incision technique. A second surgical procedure is known as a mini-open. The third procedure is an endoscopic technique.

The traditional open incision technique requires a 2 to 2½ inch incision to be made in the palm of the hand. A structure called the palmer fascia is then incised in order to reach the transverse carpal ligament. The transverse carpal ligament is then cut while making sure that the median nerve is out of the way and protected. The cut or incision may e slight (small incised amount) or drastic (e.g. as in a carpal tunnel release (CTR) procedure). Pressure on the median nerve is relieved after cutting of the transverse carpal ligament. The incised skin is then sutured. The transverse carpal ligament remains open and the gap is slowly filled by scar tissue.

The mini-open technique utilizes a 1 to 1½ cm incision proximate the transverse carpal ligament. Various types of instruments can be placed through the incision. One or more of the instruments are used to cut or incise the transverse carpal ligament from underneath as appropriate.

In the endoscopic carpal tunnel release technique, a small horizontal incision is made at the wrist and an arthroscope is introduced underneath the transverse carpal ligament. A small knife or blade, attached to the end of the arthroscope, is utilized to incise or cut the transverse carpal ligament. Again, cutting through the transverse carpal ligament alleviates the compression on the median nerve. While the endoscopic carpal tunnel release technique is less invasive than the traditional, and is typically accomplished on an outpatient basis, it is nonetheless an invasive procedure that requires time to heal.

Moreover, with current invasive techniques, the surgeon must rely on his/her own expertise for visualization, not only for the initial incision on the palm of the hand, but also in locating where dissection of the transverse carpel ligament takes place. The place of dissection is critical because while it is desired to split the transverse carpal ligament, the surgeon must not lacerate any major branch of the median or ulnar nerves.

Furthermore, although current complication rates are low (approximately 3-4%), inadvertent laceration of a nerve (either fully or partially) can have catastrophic effects on the functionality of the patient's hand, as well as impact the surgeon's practice. Because of the risks, may patients suffering from carpal tunnel syndrome forego the surgical procedure because of the involved risks. Because of the above, various instruments and/or techniques have been developed.

In U.S. Pat. No. 6,494,882 issued to Lebouitz et al. on Dec. 17, 2002, there is disclosed a cutting instrument having integrated sensors on a metal blade thereof. The blade has a recess formed therein in which is disposed a sensor element. The sensor element includes a semiconductor substrate on which is formed a sensor, sensor array and/or one or more electrodes. The sensor, sensor array and/or one or more electrodes provide a signal to circuitry on the substrate for receiving and/or conditioning the received signals. The circuitry is connected to contacts to provide a means to output signals therefrom. The Lebouitz cutting instrument, however, is only able to receive signals with respect to locating a nerve. The nerve locating signals must therefore be generated external to the cutting instrument.

In U.S. Pat. No. 5,928,158 issued to Aristides on Jul. 27, 1999, there is disclosed a medical instrument having a nerve sensor. The nerve sensor is proximate a cutting blade of the medical instrument. Electronics to generate a nerve locator signal is disposed in the medical instrument. The nerve locator signal is provided to a patient by a remote patch that is connected to the electronics via an electrical lead. The patch is applied to a strategic location on the patient.

In U.S. Pat. No. 4,962,766 issued to Herzon on Oct. 16, 1990, there is disclosed a nerve locator and evaluator. The nerve locator and evaluator is mono-polar and is thus equipped with a single electrode at the evaluation tip. The Herzon nerve locator and evaluator therefore requires a secondary wire that is attachable to a patient's body via a conductive path such as via a needle or patch.

In U.S. Pat. No. 6,312,392 issued to Herzon on Nov. 6, 2001, there is disclosed a hand-held disposable surgical nerve evaluator and locator (i.e. device). The nerve evaluator and locator includes a housing that serves as a handpiece and that accommodates a printed circuit board, a DC voltage source, and a compressed gas source. The nerve evaluator and locator device includes switches for a nerve evaluation mode and a nerve locator mode. The nerve evaluator and locator device includes first and second electrical leads that serve as a nerve locator signal source and a nerve locator signal receiver. It is unclear, however, how the two electrical leads, being so close together, can locate a nerve.

It is therefore evident from the above that the previous instruments and/or techniques are not adequate. This is especially true with respect to techniques on the transverse carpal ligament.

It should thus be appreciated in view of the above, that it is desired to have a scalpel and/or scalpel system that provides for incision path evaluation, particularly with respect to nerve location.

It should thus be further appreciated in view of the above, that it is desired to have a scalpel and/or scalpel system that provides for evaluation of the appropriateness of the tissue targeted for incision.

It should thus be yet further appreciated in view of the above that it is desired to have a scalpel and/or scalpel system that performs various forms of evaluation.

It should thus be still further appreciated in view of the above that it is desired to have a scalpel and/or scalpel system that, in addition to the performance of various evaluations of the target tissue, is operative to perform incising of the target tissue.

SUMMARY

The subject invention is a surgical scalpel, scalpel instrument and/or scalpel system (collectively, scalpel), of which may be particularly designed for use in a transverse carpal ligament surgical procedure, that performs various evaluations with respect to particular tissue or tissue structures (target or targeted tissue), and which is operative to incise the target tissue, preferably in response to the evaluations.

According to one aspect, the scalpel evaluates an incision path with respect to a nerve in the incision path, and is used to perform the incision if appropriate. In another and/or additional form, the scalpel evaluates whether the tissue is the correct or appropriate tissue. The scalpel emits an evaluation signal through the tissue captured by the scalpel. The scalpel utilizes the emitted evaluation signal to determine the presence of a nerve in the incision path and/or of the appropriateness of the captured tissue.

The scalpel preferably provides a warning if a nerve is determined or evaluated to be in the proposed incision path and/or the target tissue is inappropriate. The blade of the scalpel may also be extendable into and retractable from a body of the scalpel. Extension and/or retraction is preferably, but not necessarily, in response to the evaluation(s).

The scalpel may include an integral evaluation signal receiver or detector that is responsive to the emitted or transmitted evaluation signal. The scalpel may include, either in addition to or separate from the integral evaluation signal receiver/detector, an external evaluation signal receiver/detector that is configured to contact a patient's skin and receive and/or detect the nerve evaluation signal.

In one form, the subject invention is a method of incising a tissue structure. The method includes the steps of: (a) capturing a tissue structure of a patient in an evaluation and incision instrument; (b) evaluating an incision path through the captured tissue structure utilizing the evaluation and incising instrument; and (c) performing an incision of the captured tissue structure utilizing the evaluation and incision instrument based on the evaluation.

In another form, the subject invention is a system for performing an incision on a tissue structure. The system includes a surgical instrument configured to i) capture a tissue structure; ii) evaluate whether an incision path of the capture tissue structure is clear of a nerve, and iii) incise the capture tissue structure when the incision path of the captured tissue structure is clear of a nerve; and a control unit in communication with the surgical instrument and configured to process evaluation data obtained via the surgical instrument in order to determine whether the incision path is clear of a nerve.

In still another form, the subject invention is a surgical instrument. The surgical instrument includes a body, a channel formed in the body and open on one side thereof, the channel configured to receive target tissue for incising, and a blade disposed in the body and configured to retractably extend into the channel. The surgical instrument further includes a signal transmitter carried by the body and adapted to transmit an evaluation signal into the channel, a signal receiver carried by the body and adapted to receive the transmitted evaluation signal, and circuitry coupled to the signal transmitter and the signal receiver and adapted to control the signal transmitter, monitor the signal receiver, and evaluate an incision path through the target tissue.

In another embodiment, a surgical method includes making an opening in the skin of a patient having an orthopedic condition involving a nerve pathology producing pain, positioning an instrument in the opening, the instrument having first and second substantially opposed arcuate arms, each arm having a concave inside surface so that the arms substantially define a rounded space therebetween having an initial center point, and a third component located substantially at a periphery of the rounded space and having a distal end facing the initial center point, retaining an internal target tissue comprising a nerve on the instrument, causing an emitter to apply an emission signal upon the retained internal target tissue, causing a detector to receive an evaluation signal from the internal target tissue, wherein the evaluation signal is a tissue response to the emission signal, causing a processor to receive the evaluation signal from the detector, receiving an indicia about the nerve from the processor, and retracting the third component away from the initial center point in response to receiving the indicia.

In one or more embodiments of a surgical method, the emitter is located on the instrument.

In one or more embodiments of a surgical method, the detector is located on the instrument.

In one or more embodiments of a surgical method, the detector is remotely located.

In one or more embodiments a surgical method includes making an opening in the skin of a patient having an orthopedic condition involving a nerve pathology producing pain, positioning an instrument in the opening, the instrument including first and second substantially opposed arcuate arms, each of the first and second substantially opposed arcuate arms having a concave inside surface so that the first and second substantially opposed arcuate arms substantially define a rounded space therebetween having an initial center point, and a third component located substantially at a periphery of the rounded space and having a distal end facing the initial center point, retaining an internal target tissue comprising a nerve with the instrument, applying an emission signal upon the retained internal target tissue with an emitter, receiving a first signal from the internal target tissue with a detector, wherein the first signal is a tissue response to the emission signal, receiving a second signal from the detector with a processor, the second signal associated with the first signal, receiving an indicia about the nerve from the processor, and retracting the third component away from the initial center point in response to receiving the indicia.

In one or more embodiments of a surgical method, applying an emission signal includes applying the emission signal upon the retained internal target tissue with an emitter located on the instrument.

In one or more embodiments of a surgical method, receiving a first signal from the internal target tissue with a detector includes receiving the first signal from the internal target tissue with a detector located on the instrument.

In one or more embodiments of a surgical method, receiving a first signal from the internal target tissue with a detector includes receiving the first signal from the internal target tissue with a detector which is remotely located from the instrument.

Figure 1:
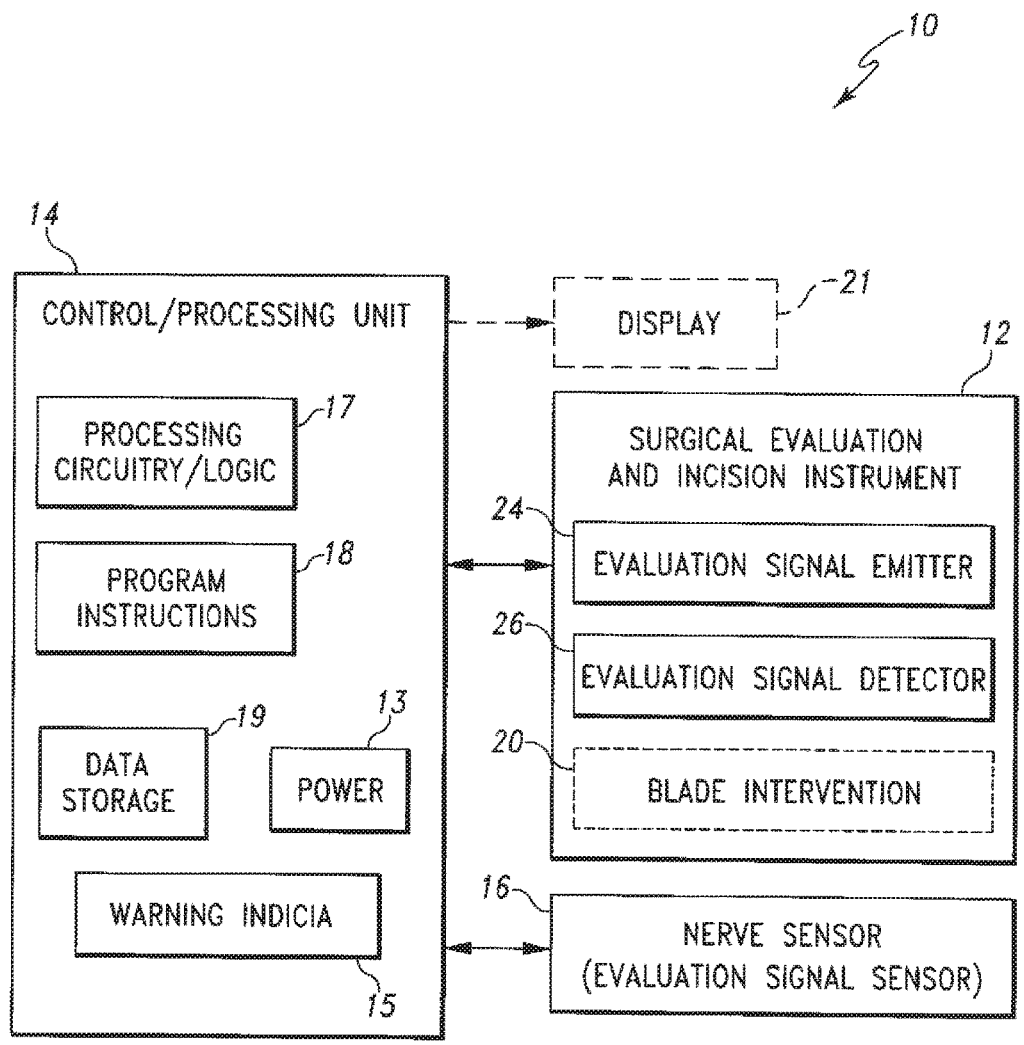
FIG. 1 is a block diagram of an exemplary embodiment of a scalpel system, method and/or apparatus for evaluating a dissection path through target tissue and for performing an incision of the target tissue in accordance with the principles of the subject invention.

Corresponding reference characters indicate corresponding parts throughout the several views. Like reference characters tend to indicate like parts throughout the several views. Different reference numbers corresponding to like terms and/or terminology tends to denote the same or similar features and/or functions with respect to the particular term and/or terminology.

DESCRIPTION OF THE PREFERRED EMBODIMENT(S)

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention.

Referring now to FIG. 1, there is shown a block diagram of a scalpel system, generally designated 10, in accordance with the present principles. Without being limiting, the scalpel system 10 is adapted, configured and/or operative to receive, capture, surround, retain, etc. an amount of tissue such as a ligament for incising an amount thereof, evaluate a proposed incision path through the tissue (i.e. target tissue), and incise the target tissue based on the evaluation. In one form, the evaluation comprises determining if a nerve is in the incision path. In another form, the evaluation comprises determining if the tissue itself is proper for incising. The scalpel system 10 preferably, but not necessarily, provides visual and/or audible feedback regarding the evaluation.

The system 10 allows the dissection/incision (collectively, incision) of the tissue with respect to the particular dissection/incision path (collectively, incision path). Particularly, the system 10 provides a system, method and/or apparatus for evaluating the appropriateness of the target tissue itself and/or an incision path through target tissue, particularly internal target tissue, of a patient and for dissecting or incising the target tissue based on the evaluation during a surgical procedure. It should be appreciated that while the present principles will be described in connection with surgery on a transverse carpal ligament of a patient, the present principles are not applicable exclusively to the evaluation and incision of the transverse carpal ligament. Thus, while the present principles are utilized in describing evaluation and/or incision with respect to the transverse carpal ligament, the present principles are applicable to evaluation and incision of other body tissue.

It should be understood that the scalpel system 10 may not necessarily include all of the components shown in the figures and/or described herein. The scalpel system 10 comprises one or more of the various components, as are necessary to carry out the present principles. Any discussion of the scalpel system thus includes its variants.

In general, the system, method and/or apparatus 10 is provided for evaluating the appropriateness of target tissue and/or a dissection or incision path through the target tissue and for dissecting or incising the target tissue based on the evaluation. The system, method and/or apparatus is particularly suited for use on a transverse carpal ligament (TCL) during a surgical procedure undertaken thereon from a small incision/dissection of a portion or part thereof up to a standard carpal tunnel release (CTR) procedure (i.e. an entire or full dissection).

The system 10 includes a surgical instrument 12 that is connected to a control or processing unit, module or the like 14. The surgical instrument 12 is adapted, configured and/or operative to receive, hold or capture tissue (e.g. a TCL) targeted for dissection or incising (i.e. target tissue) and evaluate the target tissue (itself) and/or a dissection or incision path through the target tissue before dissection/incision. Evaluation includes, but is not limited to, determining the presence of a nerve in the dissection/incision path, and/or evaluating whether the target tissue is appropriate and/or has been appropriately retained.

The control/processing unit 14 is adapted, configured and/or operative to provide control and/or similar signals to the surgical instrument 12 for operation of the surgical instrument 12 as described herein. The control/processing unit 14 is further adapted, configured and/or operative to receive evaluation and/or similar signals from the surgical instrument 12 in order to provide the functionality and/or features of the system 10 and/or scalpel 12 as described herein.

The system 10 may also include an independent nerve or evaluation signal sensor 16 that is connected to the control/processing unit 14. The nerve sensor 16 is configured, adapted and/or operative to receive or detect a nerve evaluation (evaluation) signal from a nerve and provide a nerve detection signal to the control/processing unit 14. The nerve sensor, in one form, particularly monitors a nerve or nerves for conduction of an evaluation signal input to the nerve(s) at a remote location. The remote location, in this case, is the surgical instrument 12. The control/processing unit 14 is further adapted, configured and/or operative to receive the nerve detection signal from the nerve sensor 16 in order to provide the functionality and/or features of the system 10 as described herein. Nerve sensor data, without being limiting, allows the control/processing unit 14 to determine whether the target tissue is correct and/or whether the incision path is clear for incision.

The control/processing unit 14 includes processing circuitry/logic represented by block 17. Program instructions (software or firmware) 18 may be provided for operation of the system 10. Additionally, the control/processing unit 14 may include data storage 19 in the form of a hard drive, memory or the like as necessary for storage of data, program instructions 18 as necessary, tables and/or the like. The control/processing unit 14 may operate on DC (such as via a battery or batteries) or AC electricity as appropriate, and as represented by the power box 13. In accordance with an aspect of the subject invention, warning indicia 15 is provided. Such warning indicia may be in the form of a light, lights or other visual indicia, or in the form of a sound, sounds or other audible indicia. The warning indicia 15 may be a combination of visual and audible indicia. A warning is provided to the user of the surgical instrument 12 when an evaluation determines that a nerve is in a dissection/incision path and/or when the captured target tissue itself is determined to be inappropriate. Alternatively, or in addition to the audible and/or visual warning indicia, the surgical instrument may disable extension of the blade when the evaluation determines that a nerve is in the dissection path and/or when the captured target tissue is determined to be inappropriate (as represented by the blade intervention box 20 associated with the surgical instrument 12).

A display 21 may also be provided in the system 10. The display 21 is connected to the control/processing unit 14 and is configured, adapted and/or operative to receive video signals from the control/processing unit 14 and show or present the video information. Such video information may include a visual indication of the outcome of a target tissue (dissection/incision path) evaluation (i.e. visually indicating whether there is or is not a nerve in the dissection/incision path) as well as other video information or data.

The system 10 utilizes the surgical instrument 12 to perform an evaluation of a dissection/incision path through target tissue captured by or retained in the surgical instrument. The surgical instrument 12 may perform a dissection/incision path evaluation with or without the independent nerve sensor (detector) 16 typically depending on the system embodiment. The surgical instrument 12 includes an evaluation signal emitter/transmitter or emitters/transmitters (collectively, emitter) 24 as well as an evaluation signal detector/receiver or detectors/receivers (collectively, detector) 26. The signal emitter 24 provides an evaluation signal. The signal detector 26 monitors for any portion of the evaluation signal. The emitter and detector pair may be used for evaluating the appropriateness of one or both of the captured tissue and the potential incision path.

In the case where the nerve sensor 16 is used, particularly for one aspect of evaluation, one form thereof may be a wrist band sensor, wrap sensor or similar device that is adapted to fit on the arm or wrist of the patient. The nerve sensor 16 detects evaluation signals from the ulnar and/or median nerves after an evaluation signal is applied to an upstream connecting nerve by the emitter 24 of the surgical device 12.

The emitter 24 is configured, adapted and/or operative to emit, transmit, radiate or the like, an evaluation signal. The evaluation signal is directed through the target tissue preferably, but not necessarily, under the control of the control/processing unit 14. The form of the evaluation signal and thus the emitter/detector pair but may be any such form and/or type.

The detector 26 is adapted, configured and/or operative to detect or sense any portion of the emitted evaluation signal. The detector 26 either provides a detection signal (i.e. a signal indicating that the evaluation signal has been detected) to the control/processing unit 14 when the evaluation signal has been detected, or provides the detected signal to the controller 14 for the controller to determine whether the detected signal was the evaluation signal. The control/processing unit 14 utilizes the detection and/or evaluation signal for making and/or implementing the various evaluations and/or control features/functions.

Figure 2:
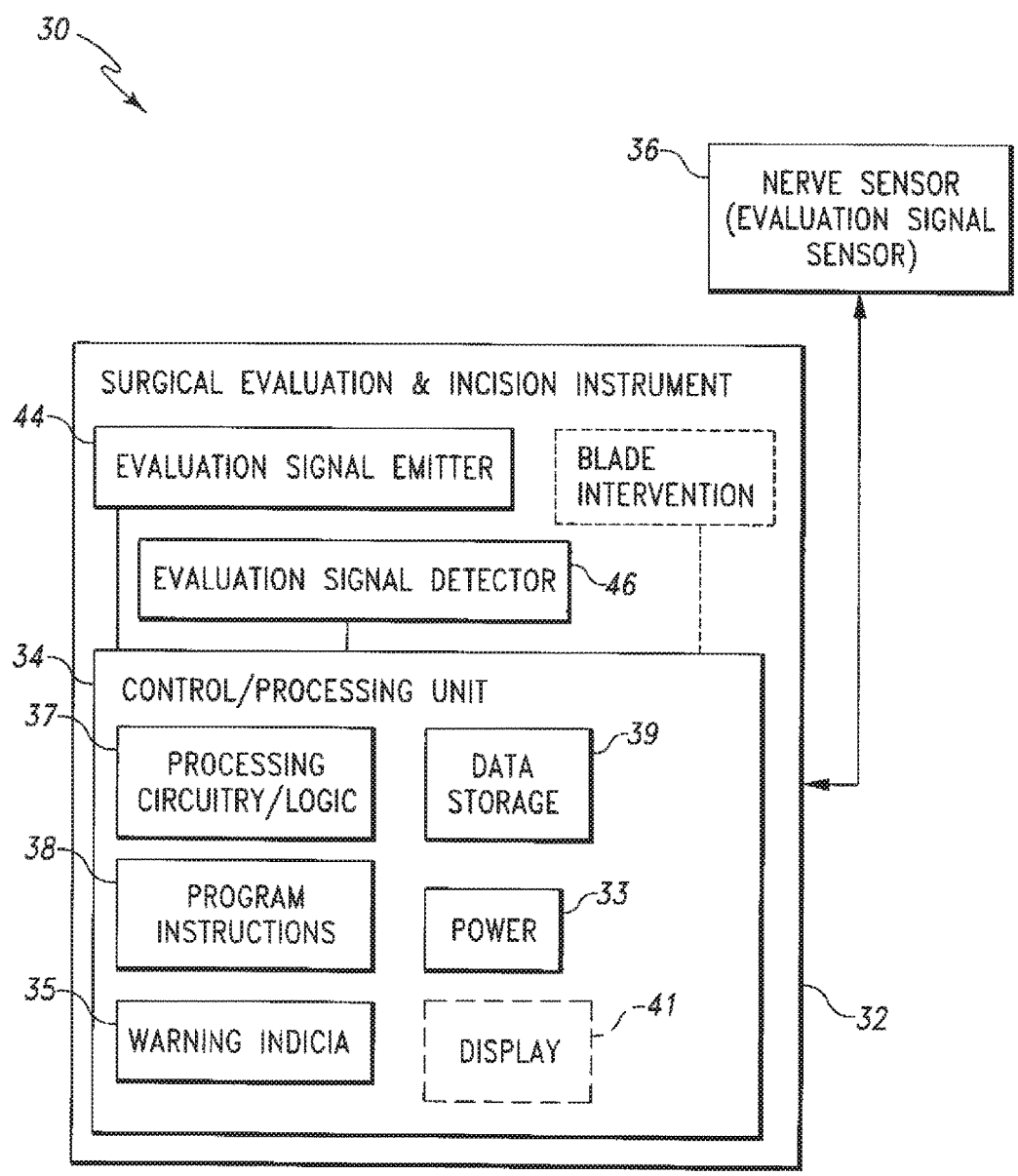
FIG. 2 is a block diagram of another exemplary embodiment of a scalpel system, method and/or apparatus for evaluating a target tissue especially a dissection path through target tissue and for performing an incision of the target tissue in accordance with the principles of the subject invention.

Referring now to FIG. 2, there is depicted another exemplary scalpel system, generally designated 30, for performing evaluation of tissue of a patient with respect to a potential dissection/incision path of the tissue in the same or like manner as the system 10. Without being limiting, the scalpel system 30 is adapted, configured and/or operative to receive, capture, surround, retain, etc. an amount of tissue such as a ligament for incising an amount thereof, evaluate a proposed incision path through the tissue (i.e. target tissue), and incise the target tissue based on the evaluation. In one form, the evaluation comprises determining if a nerve is in the incision path. In another form, the evaluation comprises determining if the tissue itself is proper for incising. The scalpel system 30 preferably, but not necessarily, provides visual and/or audible feedback regarding the evaluation.

The system 30 allows the dissection/incision (collectively, incision) of the tissue with respect to the particular dissection/incision path (collectively, incision path). Particularly, the system 30 provides a system, method and/or apparatus for evaluating the appropriateness of the target tissue itself and/or an incision path through target tissue, particularly internal target tissue, of a patient and for dissecting or incising the target tissue based on the evaluation during a surgical procedure. It should be appreciated that while the present principles will be described in connection with surgery on a transverse carpal ligament of a patient, the present principles are not applicable exclusively to the evaluation and incision of the transverse carpal ligament. Thus, while the present principles are utilized in describing evaluation and/or incision with respect to the transverse carpal ligament, the present principles are applicable to evaluation and incision of other body tissue.

In general, the system, method and/or apparatus 30 is provided for evaluating the appropriateness of target tissue and/or a dissection or incision path through target tissue and for dissecting or incising the target tissue based on the evaluation. The system, method and/or apparatus is particularly suited for use on a transverse carpal ligament (TCL) during a surgical procedure undertaken thereon from a small incision/dissection of a portion or part thereof up to a standard carpal tunnel release (CTR) procedure (i.e. on an entire or full dissection).

The system 30 includes a surgical instrument 32 that is connected to a control or processing unit, module or the like 34. The surgical instrument 32 is adapted, configured and/or operative to receive, hold or capture tissue (e.g. a TCL) targeted for dissection or incising (i.e. target tissue) and evaluate the target tissue (itself) and/or a dissection or incision path through the target tissue before dissection/incision. Evaluation includes, but is not limited to, determining the presence of a nerve in the dissection/incision path, and/or evaluating whether the target tissue is appropriate and/or has been appropriately retained.

The control/processing unit 34 is adapted, configured and/or operative to provide control and/or similar signals to the surgical instrument 32 for operation of the surgical instrument 32 as described herein. The control/processing unit 34 is further adapted, configured and/or operative to receive evaluation and/or similar signals from the surgical instrument 32 in order to provide the functionality and/or features of the system 30 and/or scalpel 32 as described herein.

The system 30 may also include an independent nerve or evaluation signal sensor 36 that is connected to the control/processing unit 34. The nerve sensor 36 is configured, adapted and/or operative to receive or detect a nerve evaluation (evaluation) signal from a nerve and provide a nerve detection signal to the control/processing unit 34. The nerve sensor, in one form, particularly monitors a nerve or nerves for conduction of an evaluation signal input to the nerve(s) at a remote location. The remote location, in this case, is the surgical instrument 32. The control/processing unit 34 is further adapted, configured and/or operative to receive the nerve detection signal from the nerve sensor 36 in order to provide the functionality and/or features of the system 30 as described herein. Nerve sensor data, without being limiting, allows the control/processing unit 34 to determine whether the target tissue is correct and/or whether the incision path is clear for incision.

The control/processing unit 34 includes processing circuitry/logic represented by block 37. Program instructions (software or firmware) 38 may be provided for operation of the system 30. Additionally, the control/processing unit 34 may include data storage 39 in the form of a hard drive, memory or the like as necessary for storage of data, program instructions 38 as necessary, tables and/or the like. The control/processing unit 34 may operate on DC or AC electricity as appropriate, and as represented by the power box 33. In accordance with an aspect of the subject invention, warning indicia 35 is provided. Such warning indicia may be in the form of a light, lights or other visual indicia, or in the form of a sound, sounds or other audible indicia. The warning indicia 35 may be a combination of visual and audible indicia. A warning is provided to the user of the surgical instrument 32 when an evaluation determines that a nerve is in a dissection/incision path and/or when the captured target tissue itself is determined to be inappropriate. Alternatively, or in addition to the audible and/or visual warning indicia, the surgical instrument may disable extension of the blade when the evaluation determines that a nerve is in the dissection path and/or when the captured target tissue is determined to be inappropriate (as represented by the blade intervention box 40 associated with the surgical instrument 32).

A display 41 may also be provided in the surgical instrument 32 such as in the form of an LCD module or the like. The display 31 is connected to the control/processing unit 34 and is configured, adapted and/or operative to receive video signals from the control/processing unit 34 and show or present the video information. Such video information may include a visual indication of the outcome of a target tissue (dissection/incision path) evaluation (i.e. visually indicating whether there is or is not a nerve in the dissection/incision path) as well as other video information or data. Other video and/or visual information may also be shown on the display 31.

The surgical instrument 32 is utilized to perform an evaluation of a dissection/incision path through target tissue captured by the surgical instrument 32. The surgical instrument 32 may perform a dissection/incision path evaluation with or without the nerve sensor 36. In this regard, the surgical instrument 32 includes an evaluation signal emitter/transmitter or emitters/transmitters as well as an evaluation signal detector/receiver or detectors/receivers (collectively, emitter) 44 as well as an evaluation signal detector/receiver or detectors/receivers (collectively, detector) 46. The signal emitter 44 provides an evaluation signal. The signal detector 46 monitors for any portion of the evaluation signal. The emitter and detector pair may be used for evaluating the appropriateness of one or both of the captured tissue and the potential incision path.

In the case where the nerve sensor 36 is used, particularly for one aspect of evaluation, one form thereof may be a wrist band sensor, wrap sensor or similar device that is adapted to fit on the arm or wrist of the patient. The nerve sensor 36 detects evaluation signals from the ulnar and/or median nerves after an evaluation signal is applied to an upstream connecting nerve by the emitter 44 of the surgical device 32.

The emitter 44 is configured, adapted and/or operative to emit, transmit, radiate or the like, an evaluation signal. The evaluation signal is directed through the target tissue preferably, but not necessarily, under the control of the control/processing unit 34. The form of the evaluation signal and thus the emitter/detector pair but may be any such form and/or type.

The detector 46 is adapted, configured and/or operative to detect any portion of the emitted evaluation signal. The detector 46 provides detection signals to the control/processing unit 34 for processing thereof as necessary. The control/processing unit 34 utilizes the detection signals for making and/or implementing the various evaluations, warnings, video, and/or control features/functions as necessary.

Figure 3:
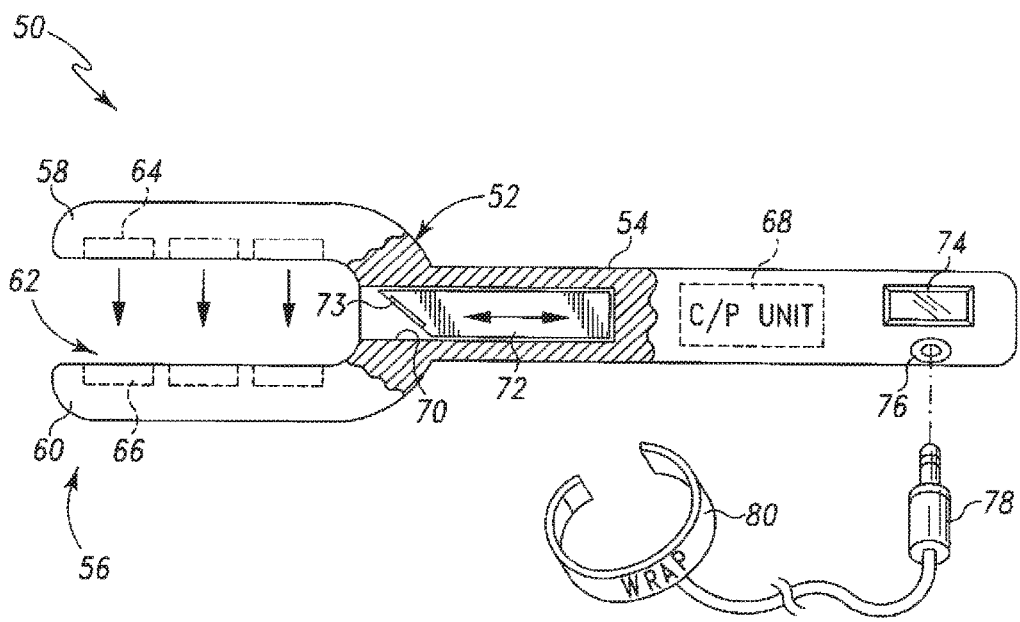
FIG. 3 is an exemplary embodiment of a scalpel and/or scalpel system in accordance with the present principles.
Figure 4:
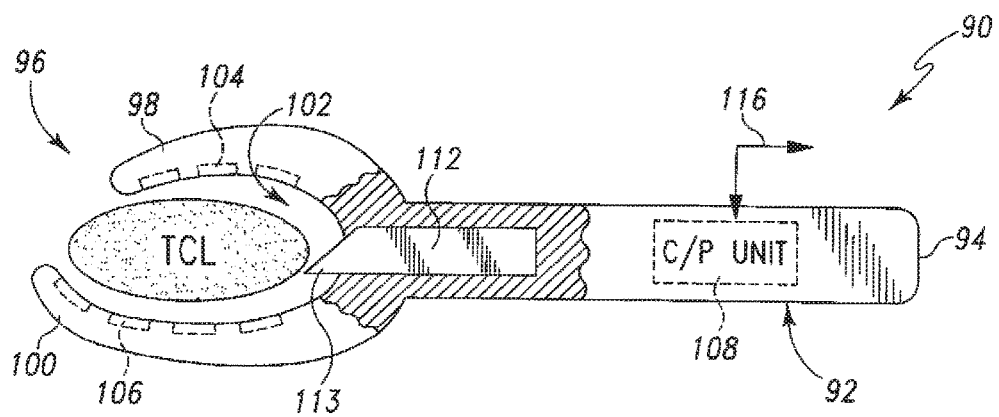
FIG. 4 is another exemplary embodiment of a scalpel and/or scalpel system in accordance with the present principles.

The systems 10 and 30 may be embodied in various designs. FIGS. 3 and 4 depict two such exemplary embodiments. While not every feature of the systems 10 and 30 is particularly shown in the embodiments of FIGS. 3 and 4, it should be understood that the embodiments of FIGS. 3 and 4 (and other embodiments) have the various features and/or functions of the systems 10 and/or 30.

Referring to FIG. 3 there is shown an exemplary embodiment of a surgical instrument or scalpel generally designated 50. The surgical instrument 50 has a body 52 that is preferably made of a metal, but may be made of a plastic, ceramic, composite and/or any other suitable surgical grade material. The body 52 has a handle or handle portion 54 in the shape of a rod. The body 52 defines a tissue reception/evaluation portion or head 56 disposed at one end of the handle portion 54. The tissue reception/evaluation portion 56 of the exemplary embodiment of the surgical instrument is in an exemplary shape of a U, tuning fork or the like and thus defines an open channel, slot or the like 62. In this embodiment, a first prong 58 and a second prong 60 define the head 56 and thus also define the tissue reception or capture area 62. Other manners of defining a reception area and/or reception area configurations in a body for the purposes of the present invention are contemplated. The tissue reception area 62 is sized to accommodate the target tissue.

The first prong 58 carries one or more evaluation signal emitters 64 each of which is in communication with a control/processing unit 68 that is here carried in the handle 54. Each emitter 64 is operative to generate or produce an evaluation signal and emit or transmit the evaluation signal into the reception area 62. The second prong 60 carries one or more evaluation signal detectors 66 each of which is in communication with the control/processing unit 68. Each detector 66 is operative to receive or detect the evaluation signal emitted by the emitter(s) 64 into the reception area 62 and/or through target tissue.

The body 52 also has a channel, slot or the like 70 that extends from a point interior to the reception area 62 to inside the handle portion 54. The channel 70 is configured to receive a blade, knife, scalpel or the like (collectively, blade) 72. The blade 72 is extendable and retractable relative to (from) the handle 54. Particularly, while the blade 72 is shown in FIG. 3 in a fully retractable position, the blade 72 is movable within the channel 70 (represented by the double-headed arrow) such that at least a portion of the blade 72 (e.g. a tip 73 of the blade 72) extends into the tissue reception area 62. In one form, the blade 72 may be manually extendable and/or retractable from and/or into the handle 54. In another form, the blade 72 may be automatically extendable and/or retractable from and/or into the handle 54. In yet another form, the blade 72 may be a combination of both manual and automatic manners of extending and/or retracting the blade 72 or blade tip/portion 73 from and/or into the handle 54.

It should be appreciated that a blade is only exemplary of a cutting means that is associated with the surgical instrument or scalpel. Thus other cutting means such as a laser, radio frequency energy, other electromagnetic energy, ultrasound and/or the like may be used in place of the blade 72. In all cases, the cutting means (collectively, "blade") is configured to be retracted, off, idle, or the like when not used and extended, on, active or the like when in use. Moreover, the blade may be carried and/or stowed in places other than the handle.

The body 52 carries a display 74 that is connected to the control/processing unit 68. Without being limiting, the display 74, preferably in the form of an LCD screen or the like, is used to provide evaluation results and/or warnings in the form of symbols, text, charts, and/or the like. The surgical instrument 50 may also provide audible warnings and/or results.

An external nerve sensor 80 in the form of a band or wrap may provide detection signals to the surgical instrument 50 via a connector 78 that is configured to be received in a receptacle 76. The receptacle 76 allows signals from the wrap 80 to be received by the control/processor 68. The control/processor may also provide signals to the wrap 80.

While not specifically shown, the surgical instrument 50 may incorporate blade intervention as discussed in connection with FIGS. 1 and 2.

Referring now to FIG. 4 there is shown another exemplary embodiment of a surgical instrument generally designated 90. The surgical instrument 90 has a body 92 that is preferably made of a plastic, but may be made of a metal or any other suitable surgical grade material. The body 92 has a handle or handle portion 94 in the shape of a rod. The body 92 defines a tissue reception/evaluation portion or head 96 disposed at one end of the handle portion 94. The tissue reception/evaluation portion 96 is curved in shape and thus defines an open channel, slot or the like 62. In this embodiment, a first curved finger 98 and a second curved finger 100 define the head 96 and thus also define the tissue reception or capture area 102. Other manners of defining a reception area in a body for the purposes of the present invention are contemplated. The tissue reception area 102 is sized to accommodate the target tissue.

The first finger 98 carries one or more evaluation signal emitters 104 each of which is in communication with a control/processing unit 108 that is here carried in the handle 94. Each emitter 104 is operative to generate or produce an evaluation signal and emit or transmit the evaluation signal into the reception area 102. The second finger 100 carries one or more evaluation signal detectors 106 each of which is in communication with the control/processing unit 108. Each detector 106 is operative to receive or detect the evaluation signal emitted by the emitter(s) 104 into the reception area 102 and/or through target tissue.

The body 92 also has a blade, knife, scalpel or the like (collectively, blade) 112. The blade 112 is preferably fixed in position, but may be extendable and retractable relative to (from) the handle 94 if desired. A tip 113 of the blade 112 extends into the tissue reception area 102. The control/processing unit 108 is connectable to other devices and/or power (if not provided for by batteries carried in the handle 94) as represented by the double-headed arrow 116.

In FIG. 4, a transverse carpal ligament (TCL) is shown as captured, received, held, retained or the like by the surgical instrument 90. It should be appreciated that while the subject invention is shown and/or described herein in connection with incising a transverse carpal ligament, (such as in a carpal tunnel release (CTR) procedure), the principles of the subject invention are applicable to other types of tissue and/or surgical procedures.

The surgical instrument 90 of FIG. 4 is ready to perform an evaluation on the TCL having already captured the TCL in the reception area 102. One or more emitters 64 provide the evaluation signal. The evaluation signal may comprise one or more evaluation signals from one or more of the emitters 104. Each evaluation signal from an emitter 104 is under control of the control/processing unit 108 such that any pattern or arrangement of evaluation signals may be emitted. Various purposes may require various patterns.

One or more of the detectors 106 receive the evaluation signal(s) as transmitted through the TCL. Each detector 106 provides a detection signal to the control/processing unit 108. Each detector/detection signal and/or a collective detection signals provides data to the control/processing unit 108.

Figure 5:
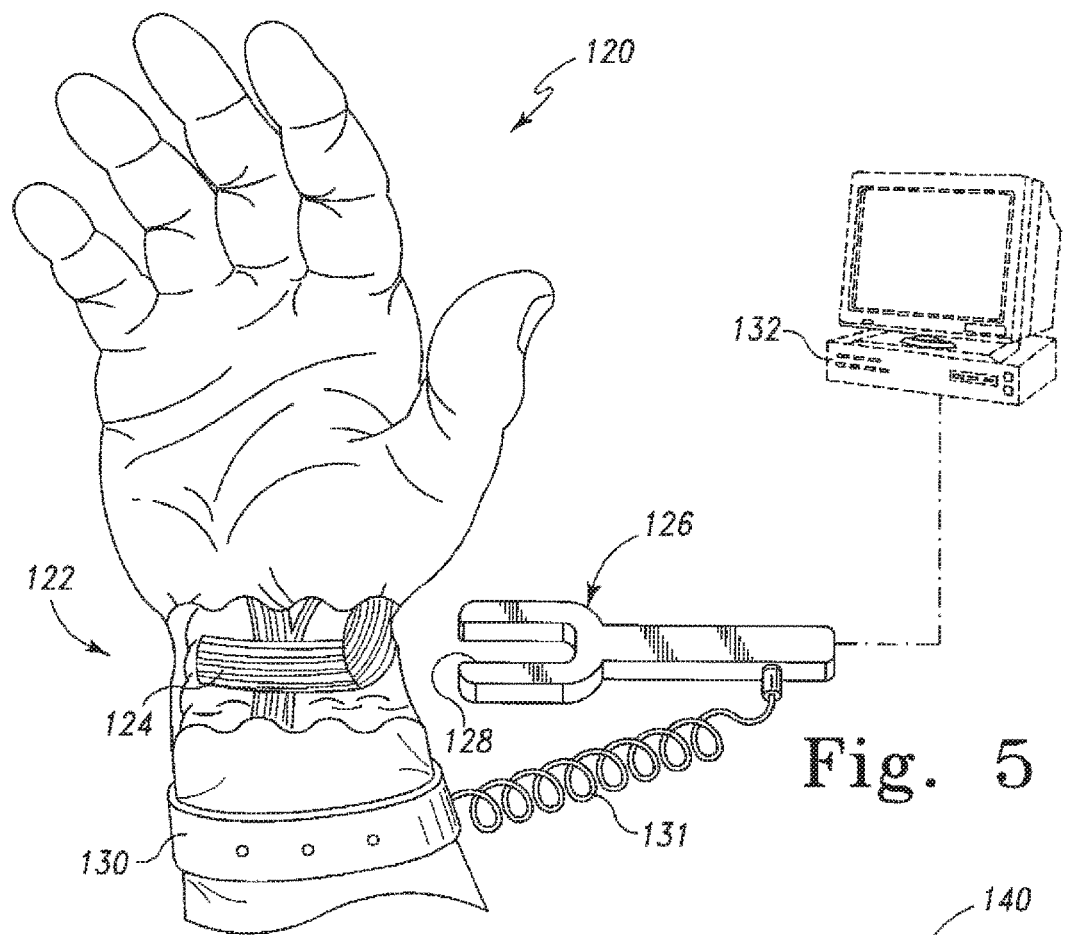
FIG. 5 is a depiction of an exemplary manner of utilizing the present invention.

Referring now to FIG. 5, there is depicted a representation of a manner of utilizing an embodiment of the surgical instrument to perform a surgical procedure, particularly a surgical procedure on a transverse carpal ligament (TCL). In FIG. 5, there is depicted a hand or upper forearm 120 of a patient. A wrist area 122 has been opened to reveal the transverse carpal ligament 124. It should be appreciated that the opening to the wrist is not intended to be a surgical guide, but is only intended for illustrative purposes. As such, the size of the opening depends on the nature of the surgical procedure and/or the size of surgical instrument 126. The surgical instrument 126, as with all of the surgical instruments described herein, may be any size overall but particularly with respect to certain portions thereof. The surgical instrument 126 may be sized according to the type of surgical procedure and/or target tissue to be incised.

The surgical instrument 126 is shown ready to capture the TCL 124 in its reception area 128. A nerve sensor wrap 130 is shown on the forearm of the patient for remotely (from the TCL and/or the surgical instrument 126) detecting nerve evaluation signals emitted from the surgical instrument 126. In this embodiment, the remote nerve sensor 130 is coupled via communication line 131 to the surgical instrument 126 (or direct to the controller). The nerve sensor 130 thus provides its nerve evaluation detection signals to the surgical instrument. The surgical instrument 126 may be coupled to a computer 132. The computer 132 or controller may receive and utilize data from the surgical instrument 126 and/or may provide control signals to the surgical instrument 126.

The nerve is thus evaluated to determine the presence of the emitted signal. The emitted signal may be in a particular pattern, form, or shape. The detector or sensor may determine whether the particular emitted signal is the received signal and provide a signal indicating same (detector does the evaluation). The detector or sensor may merely receive the signal and provide the received signal to the computer or controller for the computer or controller to make an evaluation.

Figure 6:
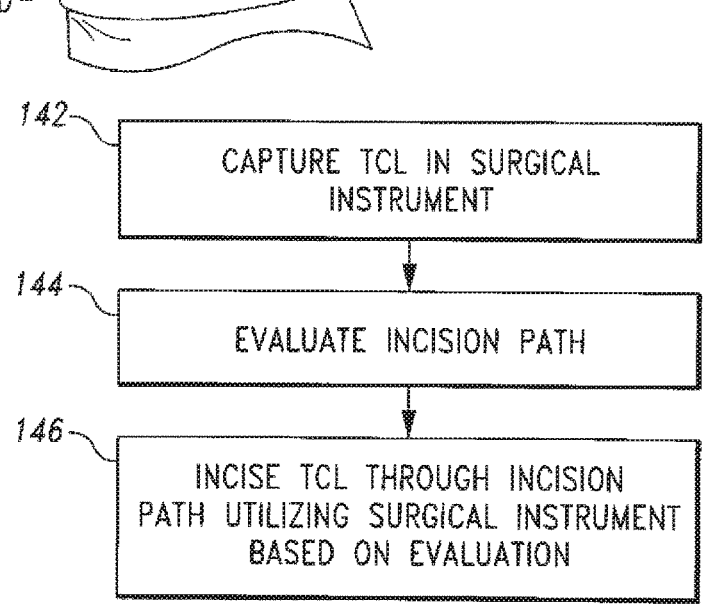
FIG. 6 is a flowchart of an exemplary general manner of utilizing the present invention, particularly by evaluating an incision path in target tissue.

Referring now to FIG. 6, there is depicted a flowchart, generally designated 140, of an exemplary manner of performing a procedure on a transverse carpal ligament in accordance with the present principles using any one of the systems described herein. It should be appreciated that while the technique is described in terms of a procedure on a transverse carpal ligament, the principles are applicable to other tissue structures.

In step 142, a transverse carpal ligament (TCL) is captured in the surgical instrument. Capturing includes, but it not limited to, holding, retaining and/or surrounding the TCL. Once captured, a prospective incision path is evaluated in step 144. The surgical instrument defines the prospective incision path. Particularly, the configuration and/or placement of the knife of the surgical instrument that is within the tissue reception area defines the incision path in the target tissue (e.g. the TCL). Evaluation of the incision path determines whether the prospective incision path is free or devoid of any nerves and/or whether the captured TCL (tissue) itself is appropriate for incising.

Thereafter, in step 146, the TCL may be incised through the incision path utilizing the surgical instrument based on the evaluation. Particularly, if it is determined by the evaluation that there is a nerve in the incision path and/or that the captured tissue is inappropriate, a warning or warnings are provided by or via the surgical instrument, and/or the blade is blocked from the ability to incise tissue or caused to not extend into the tissue reception area of the surgical instrument. If the evaluation determines that the incision path is clear of nerves and/or that the appropriate tissue (type and/or amount) has been captured, the surgical instrument is used to perform the incision.

Figure 7:
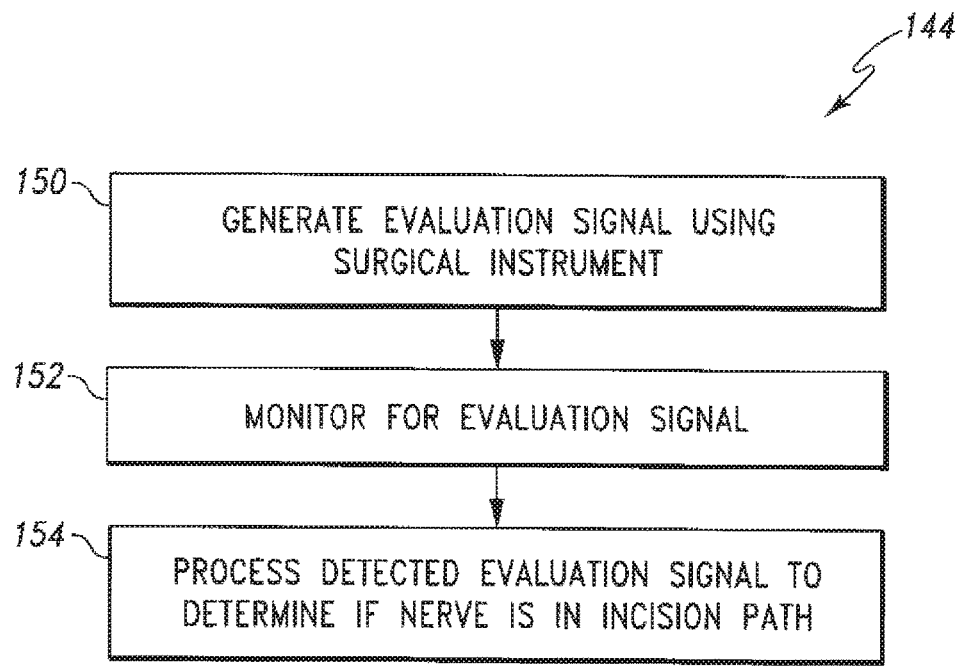
FIG. 7 is a flowchart of an exemplary manner of performing the step of evaluating an incision path of the method of FIG. 6, particularly for the determination of the presence or not of a nerve in accordance with the present principles.

FIG. 7 depicts a flowchart illustrating an exemplary manner of performing the evaluation step 144 of the flowchart of FIG. 6. It should be appreciated that the evaluation of the incision path may take various forms and/or may involve several types of evaluations. The flowchart of FIG. 7 provides one method with respect to the presence of a nerve or nerves in the incision path.

In step 150, the surgical instrument generates and emits an evaluation signal. In step 152, the emitted evaluation signal is monitored. In one form, the surgical instrument itself monitors the evaluation signal with integral detectors. In another form, an external nerve sensor is utilized that is placed on the patient. In step 154, the detected evaluation signal is the processed to determine whether a nerve is in the prospective incision path.

Figure 8:
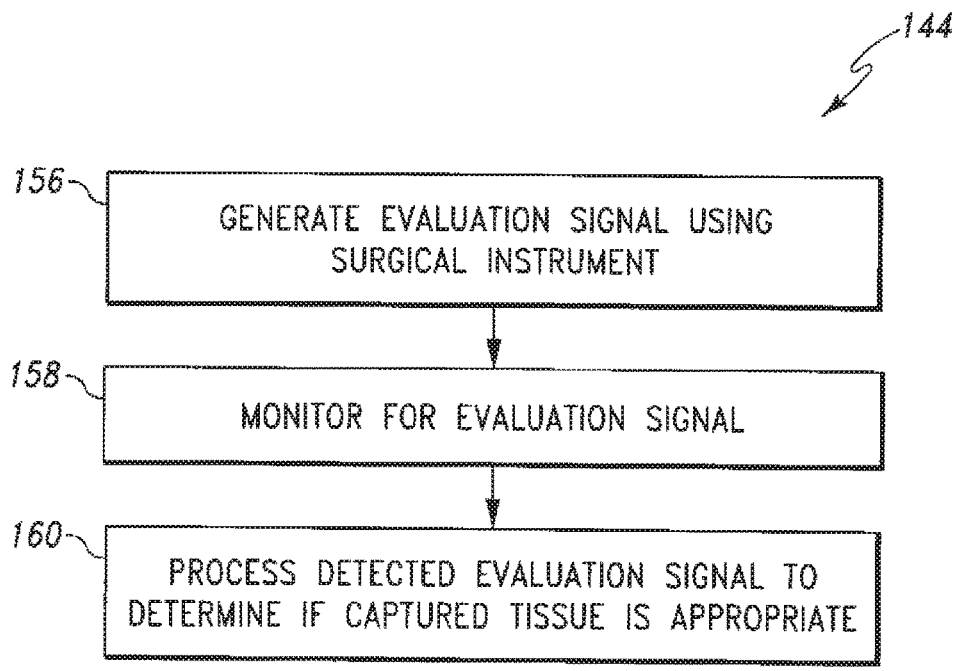
FIG. 8 is a flowchart of an exemplary manner of performing the step of evaluating an incision path of the method of FIG. 6, particularly for the determination of whether tissue captured by the surgical instrument is appropriate.

FIG. 8 depicts a flowchart illustrating another exemplary manner of performing the evaluation step 144 of the flowchart of FIG. 6. It should be appreciated that the evaluation of the incision path may take various forms and/or may involve several types of evaluations. The flowchart of FIG. 8 provides another method with respect to the presence of a nerve or nerves in the incision path.

In step 156, the surgical instrument generates and emits an evaluation signal. In step 158, the emitted evaluation signal is monitored. The surgical instrument itself monitors the evaluation signal with integral detectors. In step 160, the detected evaluation signal is the processed to determine if the captured tissue (TCL) is appropriate.

It should lastly be appreciated that the methods described in connection with the flowcharts of FIGS. 6-8 may utilize more steps or may utilize less steps than shown and/or described herein. Moreover, the sequence of steps may change.

There is a plurality of advantages of the subject invention arising from the various features of the subject invention described herein. It will be noted that further alternative embodiments of the subject invention may not include all of the features described yet still benefit from at least some of the advantages of such features. Those of ordinary skill in the art may readily devise their own implementations of the subject invention that incorporate one or more of the features of the subject invention and that fall within the spirit and scope of the subject invention.

What is claimed is:

1. A surgical method comprising:
    making an opening in the skin of a patient having an orthopedic condition involving a nerve pathology producing pain;
    positioning an instrument in the opening, the instrument having first and second substantially opposed arcuate arms, each arm having a concave inside surface so that the arms substantially define a rounded space therebetween having an initial center point, and a third component located substantially at a periphery of the rounded space and having a distal end facing the initial center point;
    retaining an internal target tissue comprising a nerve on the instrument;
    causing an emitter to apply an emission signal upon the retained internal target tissue;
    causing a detector to receive an evaluation signal from the internal target tissue, wherein the evaluation signal is a tissue response to the emission signal;
    causing a processor to receive the evaluation signal from the detector;
    receiving an indicia about the nerve from the processor; and
    retracting the third component away from the initial center point in response to receiving the indicia.

2. The method of claim 1 wherein the emitter is located on the instrument.

3. The method of claim 1 wherein the detector is located on the instrument.

4. The method of claim 1 wherein the detector is remotely located.

5. A surgical method comprising:
    making an opening in the skin of a patient having an orthopedic condition involving a nerve pathology producing pain;
    positioning an instrument in the opening, the instrument including first and second substantially opposed arcuate arms, each of the first and second substantially opposed arcuate arms having a concave inside surface so that the first and second substantially opposed arcuate arms substantially define a rounded space therebetween having an initial center point, and a third component located substantially at a periphery of the rounded space and having a distal end facing the initial center point;
    retaining an internal target tissue comprising a nerve with the instrument;
    applying an emission signal upon the retained internal target tissue with an emitter;
    receiving a first signal from the internal target tissue with a detector, wherein the first signal is a tissue response to the emission signal;
    receiving a second signal from the detector with a processor, the second signal associated with the first signal;
    receiving an indicia about the nerve from the processor; and
    retracting the third component away from the initial center point in response to receiving the indicia.

6. The method of claim 5 wherein applying an emission signal comprises:
    applying the emission signal upon the retained internal target tissue with an emitter located on the instrument.

7. The method of claim 5 wherein receiving a first signal from the internal target tissue with a detector comprises:
    receiving the first signal from the internal target tissue with a detector located on the instrument.

8. The method of claim 5 wherein receiving a first signal from the internal target tissue with a detector comprises:
    receiving the first signal from the internal target tissue with a detector which is remotely located from the instrument.

* * * * *